United States Patent [19]

Lynggaard et al.

[11] Patent Number: 5,695,719
[45] Date of Patent: Dec. 9, 1997

[54] DEVICE FOR ANALYZING A FLUID MEDIUM

[75] Inventors: Anders Lynggaard, Risskov; Ib Espensen, Nordborg; Theiss Stenstrøm, Sønderborg, all of Denmark; Bo Karlberg, Sollentuna, Sweden; Ole Ploug, Allerød, Denmark; Steen Gaardsted Kristensen, Nordborg, Denmark; Niels Eisum, Risskkov, Denmark

[73] Assignees: Danfoss A/S, Nordborg, Denmark; Tecator AB, Hoganas, Sweden

[21] Appl. No.: 553,528

[22] PCT Filed: Apr. 28, 1994

[86] PCT No.: PCT/DK94/00169

§ 371 Date: Oct. 30, 1995

§ 102(e) Date: Oct. 30, 1995

[87] PCT Pub. No.: WO94/25875

PCT Pub. Date: Nov. 10, 1994

[51] Int. Cl.$^6$ .............................. G01N 35/08; B01D 61/28
[52] U.S. Cl. ............................ 422/81; 422/63; 422/68.1; 422/1; 422/100; 422/104; 436/52; 436/174; 436/178; 436/179; 436/180
[58] Field of Search ............................ 422/68.1, 81, 63, 422/100, 104; 436/43, 52, 165, 174, 175, 177, 178, 179, 180

[56] References Cited

U.S. PATENT DOCUMENTS

| | | | |
|---|---|---|---|
| 2,913,386 | 11/1959 | Clark, Jr. | 204/415 |
| 3,733,177 | 5/1973 | Klein | 436/52 |
| 4,022,575 | 5/1977 | Hansen et al. | 436/52 |
| 4,240,912 | 12/1980 | Stumpf et al. | 210/321.2 |
| 4,837,161 | 6/1989 | Stevens et al. | 436/52 |
| 4,920,060 | 4/1990 | Parrent, Jr. et al. | 436/178 |
| 4,960,711 | 10/1990 | Aoki et al. | 436/124 |
| 4,973,561 | 11/1990 | Hansen et al. | 436/52 |
| 5,019,515 | 5/1991 | Gisin et al. | 436/52 |
| 5,037,737 | 8/1991 | Liffmann et al. | 435/11 |
| 5,389,524 | 2/1995 | Larsen et al. | 435/29 |
| 5,434,084 | 7/1995 | Burgess, Jr. | 436/52 |
| 5,525,475 | 6/1996 | Ladouceur | 435/7.9 |

FOREIGN PATENT DOCUMENTS 0047130  10/1982  European Pat. Off.

*Primary Examiner*—Long V. Le
*Attorney, Agent, or Firm*—Lee, Mann, Smith, McWilliams, Sweeney & Ohlson

[57] ABSTRACT

A fully functional analyzing unit is included within the fluid-tight housing of a dialyzer which may be immersed in the medium to be analyzed. An opening in the housing is closed by a dialysis membrane. A channel defining body cooperates with the membrane to define a flow channel. The unit includes a carrier fluid reservoir and a carrier pump for generating a flow of carrier fluid through the flow channel. By dialysis via the membrane, the flow of carrier fluid is transformed into a flow of sample fluid which is received in a reaction channel. Reagent fluid from at least one reagent reservoir is delivered to the reaction channel by at least one reagent pump, and a detecting device is coupled to the reaction channel for detecting a reaction product originating from a reaction between the reagent fluid and the sample fluid and for generating a corresponding detection signal. Effluent from the reaction channel is received in a waste reservoir. Average volume flow in the reaction channel during operation is less than 100 μl/min, allowing for at least 30 days of uninterrupted operation. The device is suitable for in situ real-time measurement of plant nutrient salts in process waters of waste water treatment plants.

7 Claims, 4 Drawing Sheets

DEVICE FOR ANALYZING A FLUID MEDIUM

The present invention relates to a device for analyzing a fluid medium, in particular a liquid.

Fluid analyzers may be used for controlling chemical and biological processes such as the treatment of sewage water. It is desirable, for example, to lower the concentrations of nutritive salts, such as nitrogen and phosphate salts, in the effluent from waste water treatment plants. Proper control of the biological processes in the plant is required. It is therefore advantageous to be able to measure the amounts of phosphate, nitrate and ammonium in the waste water as they, amongst other variables, influence on or inform about the biological processes.

Numerous patents deal with the object of analyzing fluids, especially liquids, for the presence of various analytes. The measurement methods can in principle be divided into three groups:

(1) Methods in which a sample is taken out discontinually, filtered and analyzed;

(2) On-line methods; methods in which a sample is pumped continually out of the bulk process fluid, filtered and then at regular intervals automatically analyzed;

(3) Methods being carried out in situ. Sampling and analyzing gear is entirely or partly immersed in the medium to be analyzed, or sampling is direct and analysis is carried out so close to the process, that the time between a sampling and the development of the analysis result is short enough to allow reliable, real-time control of the process.

An analyzing system for use in process control applications should enable the user to take immediate precautions; for example in waste water treatment, precautions against a suddenly increasing content of phosphates in the fluid medium. The methods in group (1) however are predominantly carried out in the laboratory which inevitably entails a delay in time from sample collection to actual analysis.

Moreover, as water samples are often analyzed spectrophotometrically, long transfer distances may present a further problem because the continuing biological activity in the samples tends to render them less representative. Even if the samples are transported quickly from the sampling site to the laboratory, the analysis results are somewhat uncertain because of problems relating to background turbidity in the samples.

Group (2) above includes UV measurements as well as ion selective electrodes and segmented flow analysis (SFA). The so-called flow injection analysis (FIA), belongs to group (2) as well as to group (1).

The segmented flow analysis (SFA) method was first described in U.S. Pat. No. 2,797,149 and No. 2,879,141, the basic principle being that the samples to be analyzed are separated from one another by air. A refinement of this technique comprising a fluid handling system is described in U.S. Pat. No. 4,853,336. This system is particularly useful for mixing liquid samples with previously separated processing liquids, such as reagents or diluents, in continuous flow analyzers. The system permits the delayed on-line mixing of different components of an analysis mixture, such as samples with reagents or diluents, as well as mixing and interaction of such components in a single conduit.

The basic FIA principle is outlined in U.S. Pat. No. 4,022,575 and No. 4,224,033. A metered amount of the sample is introduced in a moving liquid carrier flow, constituting a well-defined zone, the volume and geometry of which should be strictly reproducible. The sample zone within the carrier flow is transferred through an analysis module and detected in a suitable detection cell. In FIA the sample may be introduced directly in a predetermined amount, optionally using a valve, or it may be introduced using a system of magnetic valves, see e.g. U.S. Pat. No. 4,177,677.

Flow injection analysis requires that sample volumes be metered with great accuracy. This problem is addressed in EP published application 107 631 which describes integrated microconduits for flow analysis wherein a miniaturized system of channels is formed in a monolithic structure. A channel section is designed to be switchable between flow paths, thus allowing the metering of a sample volume by placing it in the switchable channel section while switched into sample flow, and then switching the channel section into analysis flow to process the sample volume in a batch process.

An example of an arrangement belonging to group (3) as defined above is a polarography cell, the so-called Clark cell, for direct measurement of the proportional quantity of a substance in a composition. This is described in U.S. Pat. No. 2,913,386. The cell includes a tubular body having a membrane-covered cavity wherein an anode and a cathode are arranged in a predetermined fixed spatial relation. The cavity is filled with an electrolyte. The space between the electrodes defines a "bridge" through which ions are transferred while chemical reactions take place in the electrolyte. The electrolyte is consumed in the chemical reaction and needs to be replaced frequently. The cell is suited to determine e.g. oxygen, $SO_2$ or $CO_2$ in liquids, gases or solids.

A further example belonging to group (3) above is an analyzer designated APP (Automatic Pump Photometer) which has been constructed by ME Meerestechnik-Elektronik GmbH, see the document DE C1 38 22 788. This device is specifically designed for in situ use in water to take samples, analyze the samples directly and store the results of the measurements. The APP analyzer is able to detect changes in concentrations of given substances within relatively short intervals (10–30 min.), the measurable substances being e.g. ammonium, nitrate, nitrite, phosphate, silicate, sulfide, cyanide and heavy metals. The central part of the APP analyzer is a reciprocating pump which serves also as a reaction cell and a cuvette and which aspirates the sample as well as the reagents. The liquid passes through a distributing valve, which opens and closes the different ducts for the liquids and determinates the succession of mixing steps. After each measurement the sample-reagent mixture is expelled from the apparatus.

The APP analyzer is based upon drawing a sample into the system but contains no filtration unit capable of keeping out bacteria; there is therefore a risk of bacterial growth inside the analyzer which again may cause biological activity changing the analyte concentration compared with the outside concentration. The sample must be metered precisely which appears to be rather difficult with the shown combination of pump, reaction cell and cuvette. A relatively large reagent consumption per measurement combined with the fastest cycling time (10–30 minutes) results in a time between reagent replacements of about one week. Some of the reagents used may be toxic, and the release of the sample-reagent mixture after each measurement may be a hazard to the environment as well as to the correctness of future measurements.

The present invention relates to a device of the dialyzer type. It comprises a fluid-tight housing having an opening closed by a membrane having a first and a second major surface and allowing transfer of ions and molecules between the surfaces, the first major surface in use contacting the medium to be analyzed, and further includes channel defining means in the housing fitting with the membrane to define at least one flow channel delimited by the second major surface of the membrane and by the channel defining means.

Such a device is known from the document AT 355 546. The document shows a sterilizable dialyzer for use in fermentation tanks, chemical reactors or the like. The dialyzer includes a dialyzer head covered with a dialysis membrane. The head is to be fitted in an opening in the wall of the tank or reactor. Via a feed line and a drain line in the dialyzer a suitable buffer solution is fed along the back side of the membrane while the liquid in the tank or reactor contacts the front side of the membrane. Dialysable substances present in the liquid are dialysed into the buffer solution via the membrane and transported along the drain line to an external analytical instrument or system.

In the invention as specified in claim 1, a fully functional analyzing unit is included within the fluid-tight housing of a dialyzer. The invention thus provides a self-contained unit including a carrier fluid reservoir and a carrier pump for generating a flow of carrier fluid through the flow channel to allow transfer of ions and molecules between the medium and the carrier fluid across the membrane. As a result, the flow of carrier fluid is transformed into a flow of sample fluid which is received in a reaction channel. Reagent fluid from at least one reagent reservoir is delivered to the reaction channel by at least one reagent pump, and a detecting device is coupled to the reaction channel for detecting a reaction product originating from a reaction between the reagent fluid and the sample fluid and for generating a corresponding detection signal. Effluent from the reaction channel is received in a waste reservoir.

It should be noted that in the description of this invention, the term "sample fluid" indicates a fluid which results from a process of dialysis. The sample fluid is created by an exchange of ions and molecules via a membrane; the ions and molecules are exchanged between a fluid medium, which is to be analyzed, and a carrier fluid, which is transformed into a sample fluid by the exchange; this is slightly different from common use in the chemical field where "sample" would simply denote a portion of the fluid medium to be analyzed.

This invention avoids or minimizes numerous drawbacks of the prior art. Specifically, the reliance on a process of dialysis minimizes the risk of internal pollution of the analyzing device as well as the risk of pollution of the environment. All fluids consumed and produced in the analysis are contained and retained in reservoirs within the housing. No contaminant particles or organisms will be aspirated which could disturb the measurement or cause clogging.

The device according to the invention responds very quickly to changes in the composition of the fluid to be analyzed because the analyzing unit is located within the dialyzer housing, that is, very close to the location where the actual sampling by dialysis is performed. The entire device may be immersed in the fluid to be analyzed. Reaction and detection are performed on the spot, and a detection signal indicative of the detection result is generated. The signal may be recorded within the housing for later access, such as in a monitoring application, or it may be transmitted out of the housing to a remote location for recording or further processing such as in a process control application.

The embodiment of claim 2 is particularly advantageous in process control applications. The possibility of making a valid detection of the reaction product at any time during an extended period of time allows very direct process control. Occasional calibrations and cleaning operations may be required, but the time interval between calibrations, and the time interval between cleaning operations, may be more than an hour. Deadtime between measurements is minimized, and changes in the concentration of the analyte monitored are detected with minimal time delay. Also, the detection, or "sampling" frequency may be adapted to the rate of change in the analyte concentration.

This is in distinction from batch-oriented methods such as SFA or FIA, in which the detectable reaction product arrives at the detecting device in batches, which are separated from one another either by air or by segments of carrier fluid without reaction product. In the known methods the output signal, or measurement result, of the detecting device takes the form of peaks or measurement phases, which occur when a zone of reaction product passes the detecting device, and which are separated by valleys or deadtime phases, when a zone of air or unloaded carrier fluid passes the detecting device. Detection must be synchronized with the passage of reaction product and timing restrictions are unavoidable. In contrast, in the method and the device according to claim 2, substantially no peaks or valleys, or measurement phases and deadtime phases, are observed; the flow of reaction product at the detecting device is nonsegmented and detection may be made at arbitrary times during extended intervals of time. In other words, the repetition rate of the measurement may in principle be increased arbitrarily, the only inherent limitation being in the operation of the detecting device rather than in the flow system performing the handling of the sample. For example, the detecting device may include an analog-to-digital converter having a limited repetition rate.

On the other hand, the intervals of time mentioned may be very long and comparable to or at least in the same order of magnitude as typical intervals of time over which substantial changes in analyte concentration occur in large-scale chemical or biological processes, that is, in the order of several minutes to several hours. In other words, the intervals of time may be as long as typical time constants of change in the concentration of the analyte to be monitored or measured. Thus major changes in the analyte concentration may be monitored or measured in an uninterrupted fashion.

The device according to the invention practically eliminates deadtime between measurements and minimizes the delay in time between the "sampling" at the membrane and the "measurement" at the detector; the only delay encountered is the time it takes analyte ions and molecules to travel through the flow system until they are detected in the reaction product.

It may be advantageous or even required to control the flow of the sample fluid and of one, more or all reagent fluids in the way presented in claim 3. This depends on the chemical reaction which is to be carried out in the flow, and on the detection principle to be used. In some instances it will be sufficient only to make sure that "enough" reagent is added to the flow of sample liquid to ensure complete reaction; this can be accomplished by operating with a reagent flow at a safe margin above a required minimum. In other instances, calibration of standardized reactions may require that the volume ratio of sample fluid to any reagent fluid, or between two or more reagent fluids, or both, is precisely controlled; hence the need to control flow as in claim 3.

It is advantageous to operate with flows having a Reynolds number below 5, as specified in claim 4; in such flows axial dispersion is low and if flow rates are selected to be small on an absolute scale, low consumption of reagent fluids is attainable.

Preferably the average volume flow in the reaction channel during operation is less than 100 μl/min, as specified in claim 5. This results in a low carrier and reagent consumption.

For practical purposes it is advantageous to make the volume capacity of the waste reservoir sufficient to allow at least 30 days of uninterrupted operation; replacement of the exhausted reservoirs will be required about once a month and may be conveniently planned.

The device according to the invention is especially well-suited for analyzing contaminated water in waste water purification plants as well as natural water streams, but it is also suitable for measurement and control of other fluid processes (fermentation, paper manufacturing processes, etc.). The invention is, however, in no way limited to these particular applications. Any fluid media, gases as well as liquids, may be analyzed.

It has been found that it is possible with the device according to the invention to reduce analysis response time to about one minute or less, corresponding to the time it takes analyte ions or molecules to travel from the medium to be analyzed, via the membrane, through the flow system and to the detector. It is possible to operate the device in situ so that the analyte only has to travel an extremely short distance. For example, the device may be floated in a partly immersed manner on the surface of waste water in a treatment basin.

The chemical reactions involved in the detection do not necessarily have to proceed to termination; if flow is properly controlled, the measurement can be done at any stage of the reaction since the reagent and sample mixing is reproducible. Other features contributing to the possibility of very short response times include the ability to attain an increased reaction velocity if the reaction channel is held at elevated temperature, and effective mixing if very small channel cross sections are selected.

As mentioned before it has been found that a device according to the invention may be constructed to operate for as long as an entire month or even longer in a self-contained fashion and without the necessity of service. The containers holding carrier fluid, reagent fluids, and waste fluid, are all of sufficient size to store the amount of fluid consumed or produced, respectively, over the whole period of uninterrupted operation which may be a month or more. This is possible because in liquid operation, for example, the liquid consumption may be as low as 1–10 liters per month including carrier and reagent liquids and auxiliary fluids such as cleaning agent and calibration standards. The membrane may have a comparable lifetime if properly selected to be resistant against penetration or invasion by contaminant particles and organisms.

Application of the device according to the invention as in claim 7 makes it possible to reduce the size of future waste water purification plants considerably because of the quick response of the method and device to changes in the process conditions which govern the biological processes in waste water treatment plants. Corrective action to any changes may be taken early in time, improving the overall efficiency of the biological processes and thus reducing the size of future plant or, conversely, increasing the treatment capacity of existing plant. At the same time, the amount and cost of chemicals used in water treatment, such as for precipitation of phosphate, may be reduced.

The principle of the method as well as the device according to the invention is explained in further detail below. Reference is made to the accompanying drawings in which:

FIG. 2a is a plan view of a part of a sampling cell for use in a flow system as shown in FIG. 1;

FIG. 2b and 2c are cross-sectional views of the sampling cell including the part shown in FIG. 2a;

Figure 1:
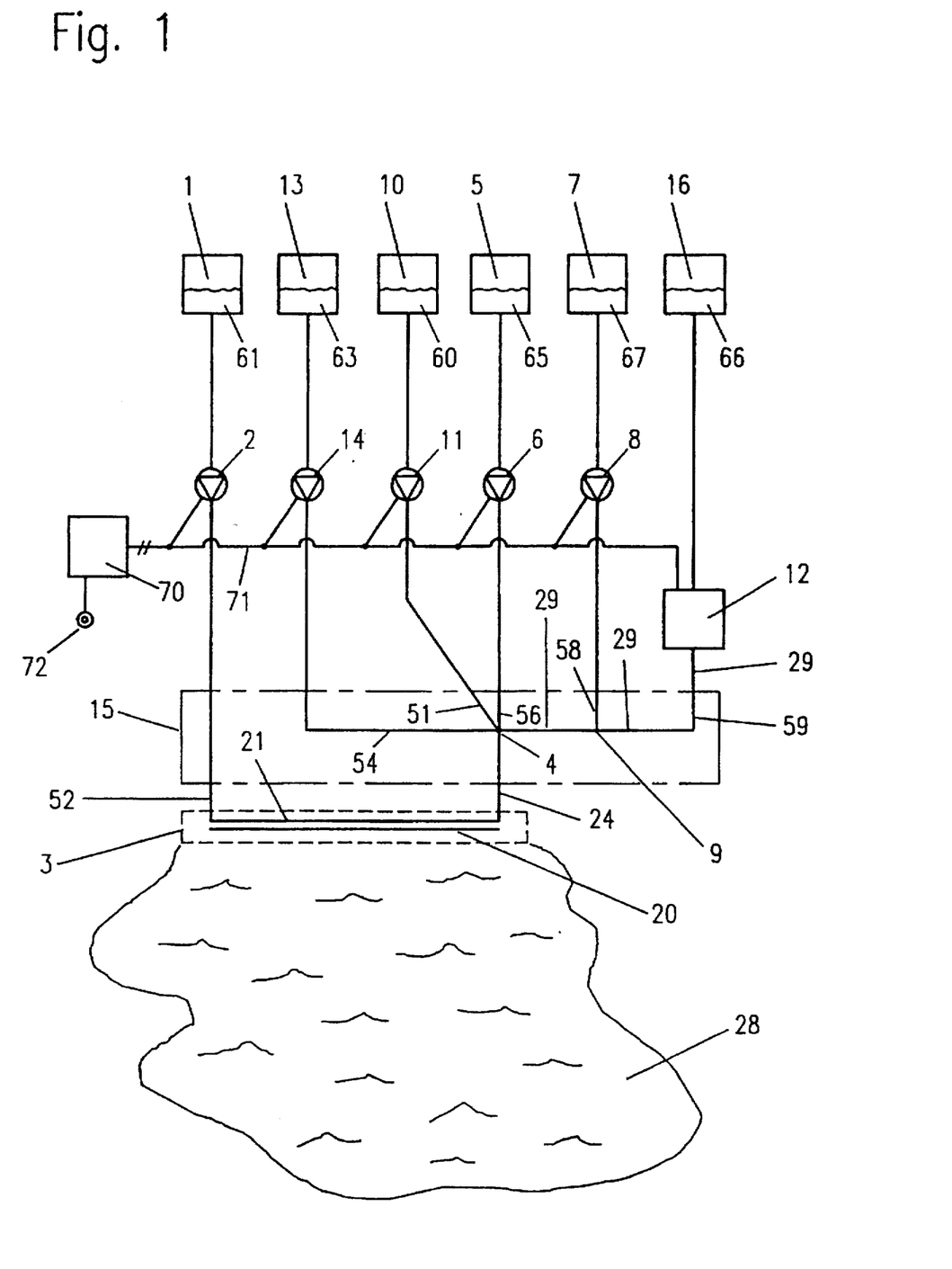
FIG. 1 is a schematic diagram of a flow system in accordance with the invention for carrying out an analysis of orthophosphate in sewage water.

FIG. 1 shows the main components of a system according to the invention which is adapted for analyzing orthophosphate in water. The main components are: liquid containers 1, 5, 7, 10, 13 and 16 for various liquids 61, 65, 67, 60, 63 and 66 to be used or produced when the system is working; pumps 2, 6, 8, 11 and 14, all controlled by a controller circuit 70 via a parallel or serial signal bus 71, for pumping the liquids through the analyzing system via channels 52, 56, 58, 51 and 54; a sampling cell 3 with a flow channel 21 and a membrane 20, in use contacting the medium 28 to be analyzed, for generating a sample liquid; a so-called flow chip 15 wherein liquids may be mixed in a controlled fashion by proper use of channels 52, 56, 58, 51 and 54 as well as channels 24, 29 and 59, and a detecting device 12 coupled to the flow chip 15 and to the controlling circuit 70 for detecting a reaction product to be analyzed. The detection result is signaled to the controlling circuit 70 for display or transmittal via remote signal bus 72.

In FIG. 1 the container 1 contains laboratory-grade demineralized water 61 which is to serve as a carrier liquid. Via channel 52 in flow chip 15 the pump 2 pumps the carrier liquid into the sample generating cell 3. In the cell 3 the carrier liquid is guided trough a flow channel 21 along the back side of the membrane 20. The flow channel is defined or delimited by the back side, or second major surface, of the membrane 20, and by a suitable mechanical device (not shown) in contact with the membrane. The front side, or first major surface, of the membrane 20 is shown to be in direct contact with the medium to be analyzed, i.e. waste water 28.

The membrane 20 is made of a material allowing transfer of ions and molecules across the membrane. This will allow the migration of ions and molecules, including orthophosphate ions, from the waste water 28 through the membrane 20 and into the flow of carrier liquid 61. As a result, the carrier liquid becomes loaded with analyte (orthophosphate) and other ions and molecules from the waste water as it flows along the flow channel 21, which transforms the carrier liquid into a sample liquid leaving the cell 3 and entering the flow chip 15 via channel 24. Of course, the use of the word "sample" in this instance differs from ordinary use in that the sample liquid in the present flow system is not a physical sample of the waste water, but rather an image of the constitution of the waste water, formed by the specific mechanism of transfer via the membrane 20 which may be diffusion.

In the flow chip 15 the sample liquid in channel 24 is led to a merging point 4 where it is combined with a flow of reagent liquid 65 from the container 5, pumped to the merging point via channel 56 by means of the pump 6. The reagent liquid 65 is a mixture of ammoniumparamolybdate (chemical constitution $((NH_4)_6Mo_7O_{24} \cdot 4H_2O)$) and potassiumantimonidetartrate (chemical constitution $KSbOC_4H_4O_6 \cdot \frac{1}{2}H_2O$) dissolved in water using sulphuric acid ($H_2SO_4$) as a dissolving aid, all in standardized concentrations according to Danish standard no. 291. The choice of chemicals is specific for a standardized method of orthophosphate analysis, requiring standardized reagents and mixing proportions.

The merging of the sample flow and the reagent flow creates a first combined flow in the reaction channel 29. While flowing along the reaction channel 29, the sample and reagent fluids in the combined flow are mixed thoroughly with each other so as to initiate a reaction between the analyte (orthophosphate ions) in the sample liquid and the reagent in the reagent liquid. A reaction product results whose concentration increases along the channel 29 as the reaction proceeds towards completion. In the present example the reaction product is a complex known as phospho-molybdic acid.

At a second merging point 9, the first combined flow is combined with a flow of a second reagent liquid 67 delivered by pump 8 via channel 58; in the present example, the second reagent liquid contains a color reagent, ascorbic acid ($C_6H_8O_6$), in a standardized concentration.

In the resulting combined flow (which may be termed the second combined flow), the first combined flow is mixed thoroughly with the second reagent to initiate a second chemical reaction. In the present example, this is a reaction between the phosphomolybdic acid produced in the first combined flow, and the ascorbic acid from the second reagent, which results in the production of a colored species, molybdenum blue, in the second combined flow while it travels along the reaction channel 29.

As indicated schematically, the reaction channel 29 runs through a detection device 12. In the present example this is a spectrophotometer for measuring the absorbance of the liquid which passes through it. The absorbance is related to the concentration of colored species in the liquid which is again related to the concentration of orthophosphate in the sample liquid produced by the sampling cell 3. That concentration is an image of the concentration of orthophosphate in the waste water 28. The whole system may then be calibrated so that the measured absorbance indicates the concentration of orthophosphate in the waste water 28.

The effluent 66 from the detecting device 12 is collected in the container 16 from which it may be discharged when necessary.

The flow system upstream of the sampling cell 3 may be calibrated at any time by using specific reference liquids 63 (only one of which is shown) of known orthophosphate concentrations fed to the merging point 4 from container 13 by means of pump 14 operating into channel 54. Pump 2 is stopped while pump 14 is operated, so as to substitute the flow of reference liquid in channel 54 for the flow of sample liquid from sampling cell 3 in channel 24. Otherwise, the device operates in the same way during calibration as explained previously for sample flow. Calibration for the whole of the detecting device, the reaction channel and the pumps is thus achieved by relating the absorbance measured during calibration to the known concentration of orthophosphate in the reference liquid 63.

As an example, if the flow resistance of the reaction channel were to change, for example because of deposits from the reagents, any resulting change in the characteristics of the system may be eliminated by such a calibration. In the same way calibration may compensate for changes in pump characteristics from wear.

In a similar fashion, the transmission characteristics of the membrane 20 may be accounted for in calibration prior to operation of the device by contacting the membrane 20 with a standard orthophosphate solution of known concentration instead of the waste water 28, operating the system as when measuring waste water, and relating the measured absorbance to the known concentration of orthophosphate in the standard solution.

The pumps 2, 6, 8, 11 and 14 are positive displacement pumps, and the controlling circuit 70 is operative to control the feed rates of the pumps so as to maintain a substantially constant ratio between the feed rates of the sample and reagent liquids. Thus a substantially constant volumetric proportion between the sample fluid and any reagent fluid is achieved at the detecting device. This will ensure that calibration is maintained.

Also, because the flow rate of each individual pump in the system can be exactly controlled, the time elapsing between the mixing of any volume element of sample liquid with a corresponding volume of reagent liquid, and the passage of the resulting mixed volume element through the detector, can be kept substantially constant. Thus it is not necessarily required that chemical reactions within the system run to completion. Calibration with known standards will ensure a valid continuous production of analysis data even on incomplete reactions. This allows for very short response times of the system.

A suitable type of pump is described in U.S. Pat. No. 2,896,459; proper control of pump operation may be achieved by driving it via an electric stepping motor controlled by a suitable control circuit. Other pump types may be used instead, and it may even be possible to use pressurized reservoirs and controlling or metering valves regulating the flows generated.

The flow system may be cleaned, if necessary, by flushing it with a cleaning liquid 60 from reservoir 10 which is delivered to merging point 4 by the pump 11 via conduit 51. All other pumps are stopped during this operation. Both calibration and cleaning of the flow system may be performed without removing the device from the analysis site.

Figures 2A, 2B, 2C:
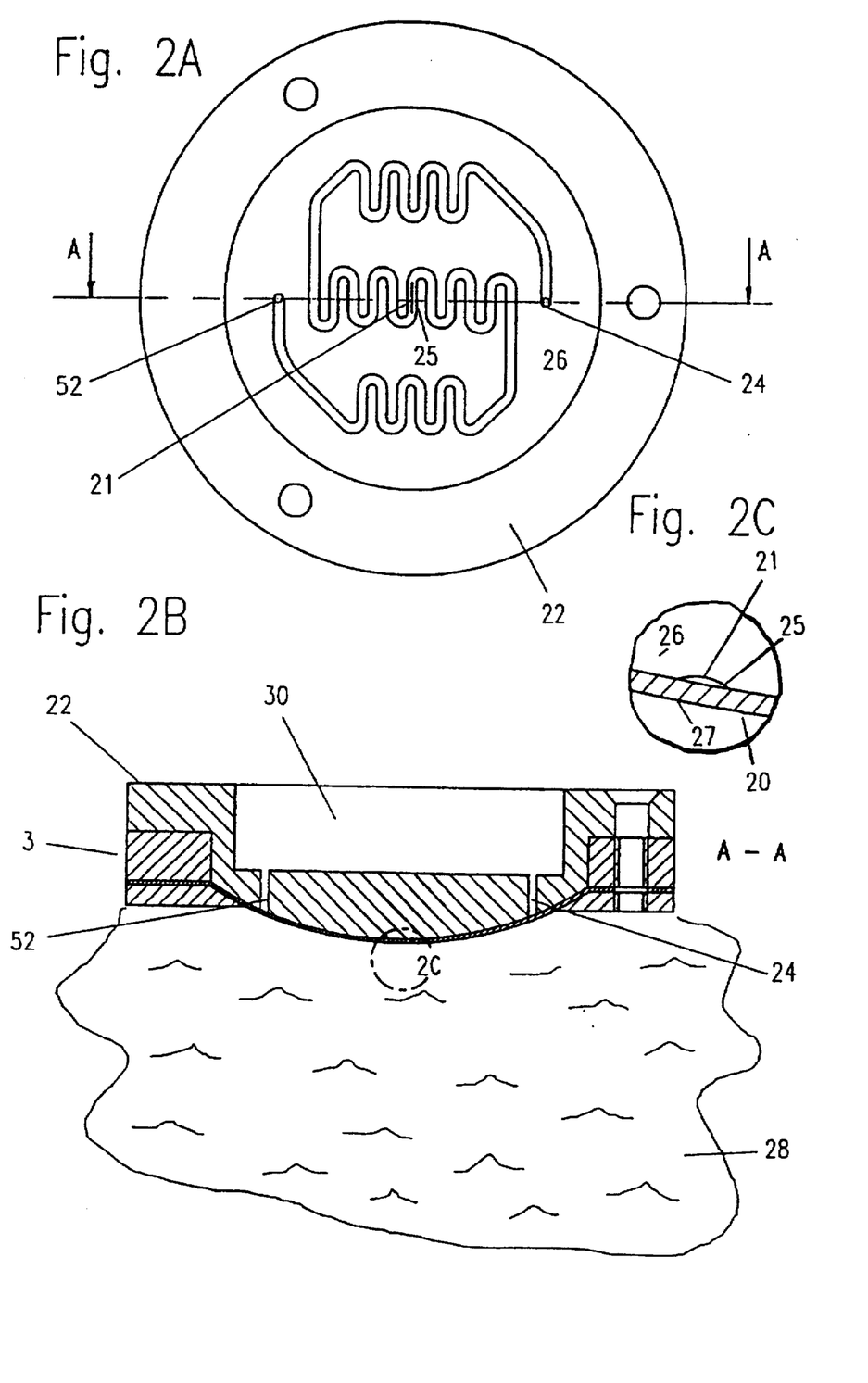

FIG. 2b is a cross-sectional view of the sample generating cell 3. The cell includes a channel defining means or support 22 fitted with the membrane 20. The support 22 is shaped generally as a disc which is formed with a meandering groove 25 (see FIG. 2a) on a surface 26 adjacent to the membrane 20. Fitted snugly to the membrane 20 as it is in use, the support 22 with groove 25 cooperates with the membrane to define a flow channel 21 of fixed shape and dimensions which is delimited by the back side of the membrane.

The surface 26 of the support 22 on which the recess is formed is hemispherical in shape except for the presence of the groove 25. The membrane 20, on the other hand, is made from plane sheet material and will become tensioned against the hemispherical surface of the support 22 when it is mounted thereon. The tensioning ensures that the membrane will not be lifted off the support 22 by the pressure which prevails in the flow channel 21 when carrier liquid is pumped through it.

If such lift-off were to occur, the various arms of the meandering flow channel 21 might short-circuit through the formation of "wild" flow paths between the membrane and the support. This would entail calibration difficulties because portions of liquid running through the wild flow paths would be in contact with the membrane 20 during a dwelling time which would be different from the dwelling time experienced by liquid portions which travel all along the flow path 21. The effect would be that the "wild" flow has generally less time to be loaded with analyte than the "ordinary" flow, causing an apparent change in the calibration of the cell 3. The convex form of the support 22 and the tensioned membrane 20 prevents this.

The flow channel 21 is shaped to have a rather large surface area covered by the membrane 20, if compared to the volume of the channel. By way of example, the groove may have a semicircular form with a width of about 1 mm and a maximum depth of about 0.13 mm, resulting in a membrane surface area to channel volume ratio of about 11/mm. Even shallower grooves may be attainable depending on the elasticity of the membrane and geometry considerations.

The membrane material is selected among materials which in all essentials only allow transfer of ions and molecules across the membrane. This may be achieved by using a membrane made from an impermeable material and subjecting it to perforation by irradiation (such membranes are commercially available under the trademark Nuclepore, amongst others) which will form very narrow channels in the membrane. Other suitable semipermeable membranes are known to workers in the fields of dialysis and osmosis.

Suitable membrane materials include cellulose acetate, teflon, regenerated cellulose acetate, polycarbonate and polyester. Materials like ceramics, for example $Al_2O_3$, may also be suitable as membrane materials.

Optionally the membrane can be covered with a permeable protective matrix placed in such a way that the protective matrix is contacting the medium to be analyzed, that is, on the front side or first major surface 27 of the membrane. An example of a suitable protective layer is fiber layer such as filtration paper. Such a coverage may prevent abrasion or other detrimental effects brought about by swelling of the membrane in water.

The overall thickness of the membrane is preferably about 5–250 μm, especially about 25 μm. Pores in the membrane are preferably about 0.01–0.45 μm in size, especially about 0.025 μm. This small pore size prevents dirt particles, bacteria, spores of funghi and possibly even large organic molecules from entering the flow system, thus preventing continuing biological activity in the analysis system. It is preferred to select the material of the membrane so as to prevent transfer of particles from the medium to be analyzed which exceed the size of analyte ions or molecules by a factor ten or more.

The support 22 is provided with through-going bores 52 and 24 which connect the flow channel 21 to other parts of the flow system. Bore 52 leads to the pump 2 for delivering carrier liquid 61, and bore 24 leads to the merging point 4 in flow chip 15.

Figure 3:
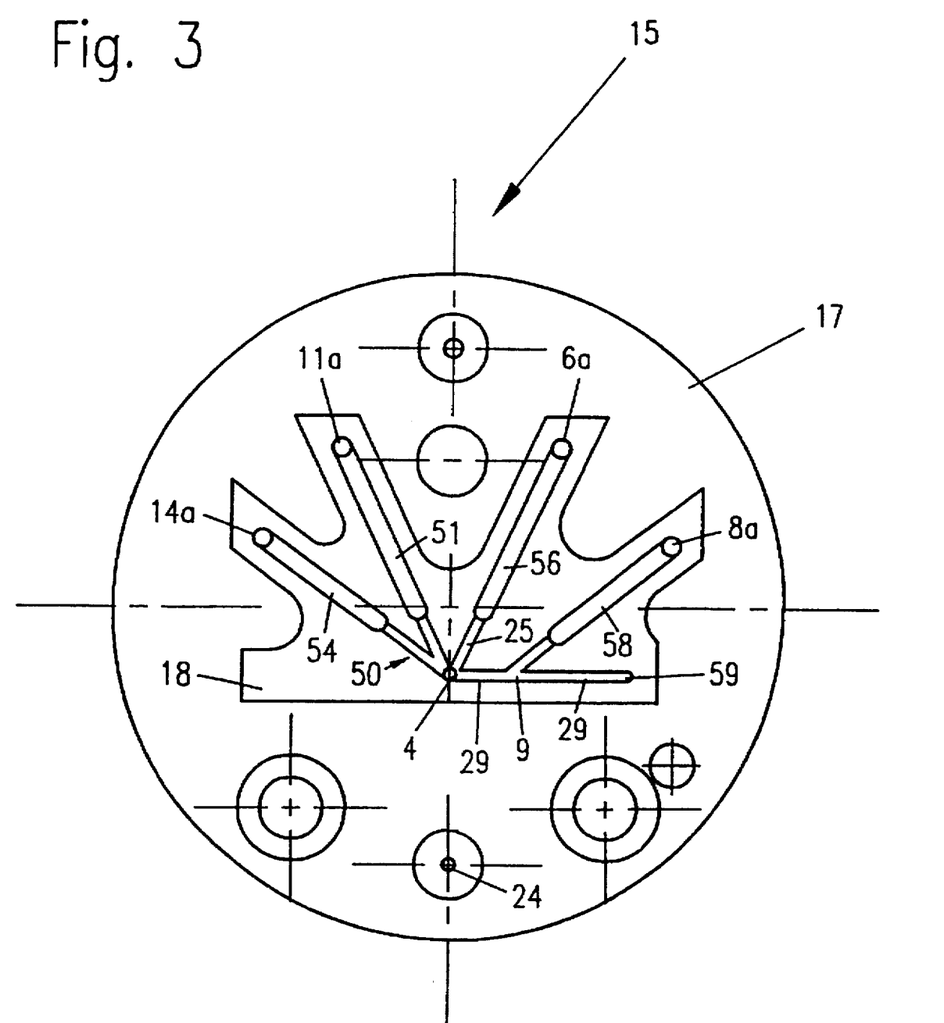
FIG. 3 is a plan view of a so-called flow chip baseplate serving as a part of the flow system shown in FIG. 1.

FIG. 3 shows a plan view of a baseplate 17 defining part of the flow chip 15.

A major portion of the flow system is formed as grooves in the baseplate 17. The baseplate is generally disc-shaped with a central elevated portion 18 on its front face which is shown in the drawing. A system 50 of grooves is engraved in the central portion 18 of the baseplate. In use the baseplate is covered with an elastomeric sheet (not shown) which covers all of the central portion 18, and the baseplate is fitted into the recess 30 (see FIG. 2B) in the sampling unit 3 in such a way that the elastomeric sheet is sandwiched between the baseplate 17 and the support 22. The elastomeric sheet thus serves as a lid or seal for the grooves 50 so as to transform the system of grooves 50 into a system of ducts or channels. Accordingly, the terms "groove" and "channel" will be used interchangeably in the following description. Connections to the grooves from other parts of the flow system are generally made via bores extending through the baseplate from front to back.

Sample liquid from the sampling cell 3 is led to the back side of the baseplate 17 through bore 24 and flows along a channel on the back (not shown) to bore 25. Via bore 25 the liquid returns to the front side of the baseplate, where it enters reaction channel or groove 29 at merging point 4.

Part of the groove system 50 are three grooves 51, 54 and 56 extending between the merging point 4 and bores 11a, 14a and 6a, respectively. Groove 51 is connected to pump 11 via bore 11a, groove 54 is connected to pump 14 via bore 14a and groove 56 is connected to pump 6 via bore 6a. Accordingly, those grooves feed first reagent liquid (groove 56), reference liquid (groove 54) and cleaning liquid (groove 51) to the merging point if their corresponding pumps are operated.

The reaction groove 29 extends between the merging point 4 and an exit bore 59 leading to the back side of the baseplate. On its way it meets a groove 58 at the second merging point 9 from which the groove 58 extends to a bore 8a connecting it with the pump 8. The second merging point 9, being the point where the groove 58 opens into the reaction channel 29, is spaced apart from the first merging point 4.

As will be apparent from the drawing, the groove layout corresponds to the schematic diagram of FIG. 1. At the merging point 4 the sample flow is combined with the first reagent, and at merging point 9 it is combined with the second reagent. The reaction products described in connection with FIG. 1 are developed while the fluids travel along the two segments of the reaction channel 29, between the first and second merging points and after the second merging point.

The detecting device, which is not shown in FIG. 3, is mounted in the immediate vicinity of the back side of the flow chip baseplate 17, near the bore 59. In proper terms the bore 59 and any additional ducting leading up to the detecting device are to be considered part of the reaction channel 29, as any chemical reactions proceeding while the liquid travels along those ducts may still influence the reading taken by the detecting device.

The grooves 51, 54, 56 and 58 as shown in FIG. 3 each have a narrow portion near the respective merging points and a wide portion near the respective bores connecting them to the pumps; the wide portions are made to reduce pressure drops. Other details shown in FIG. 3 are for mounting and auxiliary purposes which are no part of the invention.

The dimensions of the reaction channel 29 are chosen to ensure that the combined flow is laminar and has a low Reynolds number Re, preferably below 5 in average. This is done by selecting the transverse dimensions of the reaction channel relative to the viscosity ranges of the liquids involved and to the range of flow rates used in the system.

The Reynolds number Re is defined as:

$$Re = (V * D_h)/\nu,$$

wherein V is the average flow velocity, $D_h$ is the hydraulic diameter of the channel carrying the flow, defined as $D_h = 4*$ (A/P) with A denoting the cross-sectional area of the channel and P denoting the length of its perimeter, and $\nu$ is the kinematic viscosity of the fluid.

As an example, a practical system was realized wherein the reaction channel was formed as a rectangular groove in the baseplate 17, having a depth of about 0.4 mm and a width of about 0.5 mm which was closed by an essentially flat lid mounted on the baseplate, resulting in a hydraulic diameter of $D_h = 0.44$ mm. The sample and reagent liquids were essentially water, having a kinematic viscosity $\nu = 1.004$ $mm^2/sec$ at a temperature of 20 degrees Centigrade. Flow rates in the reaction channel were selected to be between 0 and about 45 μl/min, resulting in flow velocities V between 0 and 3.75 mm/sec. Accordingly, the Reynolds number of the flow varied between 0 and 1.64.

For the detection of other analytes the overall design of the flow system as well as the mechanical layout of the channel system in the flow chip 15 will normally have to be specifically adapted to the chemistry involved in the detection. Such adaptations include the provision of additional containers, pumps and channels for additional reagents, adjustments of the length of parts or all of the reaction groove 29 and the spatial relation of merging points so as to allow sufficient flow time for reactions, and other modifications.

Figure 4:
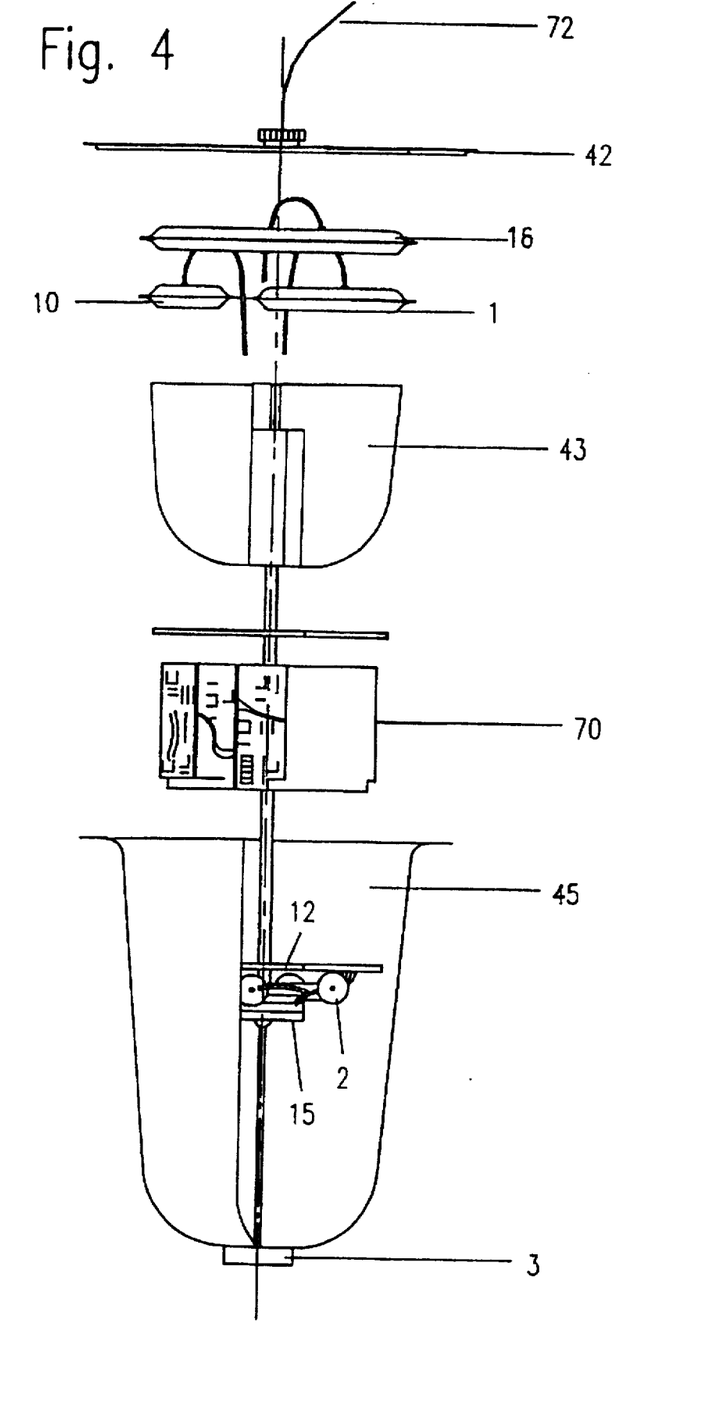
FIG. 4 is an exploded view illustrating the general layout of a self-contained, submersible device according to the invention for performing in situ analysis of waste water.

FIG. 4 illustrates one of many possible ways of housing and partitioning a device according to the invention. The upper part of FIG. 4, immediately just below a lid 42, by way of example shows containers 16, 1 and 10 placed in a reagent compartment 43 to ensure that any leak from the containers does not disturb operation or even damage the rest of the system. The control circuit 70 for controlling the system and for receiving/transmitting input and output signals via remote signal bus 72 is placed below the reagent compartment. Pumps 2,6,8,11,14 and detector 12 are located below the control circuit 70; the sampling or dialysis cell 3 is fitted in the bottom of a common housing 45 which holds all other parts and may be sealed tightly by the lid 42.

Power supply and all communication (input/output) to the system is via the remote bus 72. An output signal from the system, for example representing the amount of phosphate in waste water read by the detector, could be evaluated in a remote control unit (not shown) coupled to the remote bus 72 for controlling a waste water plant in response to signals from the analysis system. If the amount were too high, the necessary steps to reduce the amount measured could be initiated at once. In the same way it is possible via remote bus 72 to deliver input signals to the system for example to start a calibration procedure.

We claim:

1. A self-contained, immersible device for analyzing a fluid medium, comprising:

a fluid-tight housing;

an opening in the housing, the opening being closed by a membrane, the membrane having a first outer surface and a second inner surface and being formed to allow transfer of ions and molecules between the surfaces, the first outer surface being for contacting the medium;

channel defining means in the housing, the channel defining means being joined to the membrane to define at least one flow channel delimited by the second inner surface of the membrane and by the channel defining means;

a carrier fluid reservoir within the housing, the carrier fluid reservoir holding a carrier fluid;

carrier pump means within the housing, the carrier pump means being coupled to said flow channel to generate a flow of carrier fluid through the flow channel to allow transfer of ions and molecules between the medium and the carrier fluid across the membrane, whereby the flow of carrier fluid is transformed into a flow of sample fluid;

a reaction channel within the housing, the reaction channel being formed to receive the flow of sample fluid;

at least one reagent reservoir within the housing, the reagent reservoir holding a reagent fluid;

at least one reagent pump means within the housing, the reagent pump means being coupled to the reaction channel to deliver a flow of reagent fluid to the reaction channel;

a detecting device within the housing, the detecting device being coupled to the reaction channel for detecting a reaction product and for generating a corresponding detection signal; and at least one waste reservoir within the housing, the waste reservoir being coupled to receive fluid from the reaction channel.

2. A device as in claim 1, in which the pump means are operative to generate substantially nonsegmented flows such that a valid detection of the reaction product is made at any time during an extended period of time.

3. A device as in claim 1, including controlling means coupled to the pump means for controlling the flow of the sample fluid and the reagent fluid to provide a substantially constant volumetric proportion between the sample fluid and the reagent fluid at the detecting device.

4. A device as in claim 1 in which the reaction channel has a cross-sectional area and transverse dimensions, the cross-sectional area and the transverse dimensions of the reaction channel being selected relative to kinematic viscosity of the fluid in the reaction channel and to volumetric flow rate in the reaction channel so as to provide a flow in the reaction channel having an average Reynolds number less than 5.

5. A device as in claim 1, in which average volume flow in the reaction channel during operation is less than 100 µl/min.

6. A device as in claim 1, in which volume capacity of the waste reservoir is sufficient to allow at least 30 days of uninterrupted operation.

7. The use of a device as claimed in claim 1 for in situ real-time measurement of plant nutrient salts in process waters of waste water treatment plants.

* * * * *